United States Patent
Ishida et al.

(10) Patent No.: US 7,045,667 B2
(45) Date of Patent: May 16, 2006

(54) PROCESS FOR PRODUCING CYCLOALKANOL AND/OR CYCLOALKANONE

(75) Inventors: Hajime Ishida, Niihama (JP); Naoki Miura, Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/949,306

(22) Filed: Sep. 27, 2004

(65) Prior Publication Data
US 2005/0070742 A1    Mar. 31, 2005

(30) Foreign Application Priority Data
Sep. 29, 2003    (JP)    ............... 2003-337255

(51) Int. Cl.
*C07C 35/08*    (2006.01)
(52) U.S. Cl. ...................... 568/836; 568/338
(58) Field of Classification Search ............... 568/836, 568/360, 338
See application file for complete search history.

(56) References Cited

U.S. PATENT DOCUMENTS

| 4,902,827 A | * | 2/1990 | Steinmetz et al. | ........ 562/543 |
| 5,426,237 A | | 6/1995 | Murahashi et al. | |
| 5,958,821 A | | 9/1999 | Ishii et al. | |
| 6,479,705 B1 | * | 11/2002 | Murata et al. | ........... 568/320 |

FOREIGN PATENT DOCUMENTS

| WO | WO 02/090309 A1 | 11/2002 |
| WO | WO 03/099755 A1 | 12/2003 |

* cited by examiner

*Primary Examiner*—Michael L. Shippen
(74) *Attorney, Agent, or Firm*—Sughrue Mion, PLLC

(57) ABSTRACT

A process for producing a cycloalkanol and/or a cycloalkanone is provided, the process comprising the step of oxidizing cycloalkane with molecular oxygen in the presence of a mixture of metal oxides and/or a composite metal oxide, each containing cerium and zirconium as the metal elements therein.

5 Claims, No Drawings

PROCESS FOR PRODUCING CYCLOALKANOL AND/OR CYCLOALKANONE

BACKGROUND OF THE INVENTION

1. Field of the Invention

The present invention relates to a process for producing a cycloalkanol and/or a cycloalkanone by oxidizing cycloalkane with molecular oxygen.

2. Description of the Related Art

It is known that a cycloalkane can be oxidized with molecular oxygen using an oxide of a transition metal as a catalyst. For instance, Japanese Patent Application Laid-Open No. 5-310601 discloses that the above-mentioned oxidation is conducted in the coexistence of an aldehyde and a transition metal oxide containing manganese, iron, cobalt, nickel, copper, ruthenium, or osmium as its transition metal element. In addition, Japanese Patent Application Laid-Open No. 8-28909 discloses that the above-mentioned oxidation is conducted in the coexistence of an N-hydroxy cyclic imide and a transition metal oxide containing samarium, titanium, chromium, manganese, iron, ruthenium, cobalt, rhodium, or copper as its transition metal element.

In the former method, an aldehyde to be used therein is oxidized to produce the corresponding carboxylic acid as by-product. Therefore, the separation and recovery step of the product after the reaction is complicated, thereby leading to be unsatisfactory in terms of cost. Also, in the latter method, an N-hydroxy cyclic imide to be used therein easily decomposes during the reaction. Therefore, the method is also unsatisfactory from the viewpoint of operationality and cost.

SUMMARY OF THE INVENTION

Hence, the present inventors have earnestly studied to develop a process for oxidizing a cycloalkane without using a third compound such as an aldehyde and an N-hydroxy cyclic imide, and have consequently found that, when a mixture of oxides of cerium and zirconium or a composite oxide of cerium and zirconium or the like is used as a catalyst, the aforementioned object can be attained to produce a cycloalkanol and/or a cycloalkanone. The present invention has been accomplished based on such findings.

The present invention provides a process for producing a cycloalkanol and/or a cycloalkanone, the process comprising the step of oxidizing cycloalkane with molecular oxygen in the presence of a mixture of metal oxides and/or a composite metal oxide, each containing cerium and zirconium as the metal elements therein.

In accordance with the present invention, a cycloalkane can be oxidized in a good operative and cost-effective method to produce a cycloalkanol and/or a cycloalkanone with a large selectively thereto.

DESCRIPTION OF THE PREFERRED EMBODIMENTS

In the present invention, a cycloalkane is oxidized with molecular oxygen in the presence of a metal oxide catalyst, to produce the corresponding cycloalkanol and/or cycloalkanone.

Examples of the cycloalkane as the starting material include monocyclic cycloalkanes with no substituent on the ring, such as cyclopropane, cyclobutane, cyclopentane, cyclohexane, cycloheptane, cyclooctane, cyclodecane and cyclooctadecane; polycyclic cycloalkanes such as decalin and adamantane; cycloalkanes with a substituent on the ring, such as methylcyclopentane and methylcyclohexane; and the like. Two or more of them can be used together, if needed.

An oxygen-containing gas can be used as a source of the molecular oxygen. The oxygen-containing gas may be air or pure oxygen, which may or may not be diluted with an inert gas such as nitrogen, argon, or helium. Alternatively, oxygen-enriched air, which can be obtained by adding pure oxygen to the air, may be used as the oxygen-containing gas.

In the present invention, a mixture of metal oxides and/or a composite metal oxide, each containing cerium and zirconium as the metal elements therein is/are utilized as a catalyst for oxidizing a cycloalkane with molecular oxygen. Such composite and mixture metal oxides have high oxidation activities enough to oxidize the cycloalkane with molecular oxygen even when an aldehyde or an N-hydroxy cyclic imide is not utilized together, as used in the above-described conventional methods. Due to such composite and mixture metal oxides as catalyst, the oxidation of a cycloalkane can be carried out with a good operationality and in a cost-effective manner.

The aforementioned composite and mixture metal oxides can be selected from the group consisting of:
  a mixture of cerium oxide and zirconium oxide;
  a composite metal oxide of cerium and zirconium; and
  a mixture of said composite metal oxide and at least one metal oxide selected from cerium oxide and zirconium oxide.

The molar ratio of the cerium to the zirconium (i.e., cerium/zirconium), each contained in the aforementioned composite and mixture metal oxides, may be 100/1 to 1/100, and is preferably 10/1 to 1/10. The composite and mixture metal oxides may be used with being carried on (or diluted with) a carrier (or diluting agent) such as silica or alumina, if needed.

Examples of the catalyst to be used in the present invention include a mixture prepared by mechanically blending cerium oxide and zirconium oxide, a composite metal oxide of cerium and zirconium (e.g., a solid solution of cerium oxide and zirconium oxide) and the like. From the standpoint of catalyst activity, a solid solution of cerium oxide and zirconium oxide is preferable. The solid solution of cerium oxide and zirconium oxide can be produced by obtaining a coprecipitate of cerium and zirconium by means of so-called coprecipitation method and calcinating the resultant coprecipitate. More specifically, the solid solution can be produced, for example, by a method comprising the steps of dissolving a water-soluble cerium salt and a water-soluble zirconium salt to obtain an aqueous mixture solution thereof, controlling the pH of the solution to obtain a coprecipitate of cerium and zirconium and subsequently calcinating the coprecipitate.

The degrees of solid solubility of cerium oxide and zirconium oxide in the above-mentioned solid solution can be confirmed by X-ray diffraction (XRD). For instance, in XRD with copper $K_\alpha$ radiation, cerium oxide with no solid-solution property, zirconium oxide with no solid-solution property and a solid solution of cerium oxide and zirconium oxide show specific peaks at $2\theta=28.8\pm0.1°$, at $2\theta=28.2\pm0.1°$ and at $2\theta=29.2\pm0.1°$, respectively, and therefore, the degrees of solid solubility can be confirmed from these peak area ratios. Specifically, when the degree of the solid solubility of cerium oxide is expressed with the calculated value of [(peak area of $2\theta=29.2\pm0.1°$)/[(peak area of 2θ=29.2±0.1°)+(peak area of 2θ=28.8±0.1°)]]×100, then the degree of the solid solubility of cerium oxide is preferably about 10% or more, and is more preferably about 50% or more. Also, the degree of the solid solubility of zirconium oxide is expressed with the calculated value of [(peak area of 2θ=29.2±0.1°)/[(peak area of 2θ= 29.2±0.1°)+(peak area of 2θ=28.2±0.1°)]]×100, then the solid solubility of zirconium oxide is also preferably about 10% or more, and is more preferably about 50% or more.

In addition, the above-mentioned composite and mixture of metal oxides may have BET specific surface areas of from about 1 m²/g to about 300 m²/g, and preferably have BET specific surface areas of from about 10 m²/g to about 200 m²/g.

The above-mentioned composite and mixture of metal oxides may be subjected to reduction treatment prior to being used for the oxidation as a catalyst, thereby enhancing the catalyst activity thereof. The reduction treatment is preferably carried out with a hydrogen-containing gas. For example, the treatment may be conducted in a manner such that the composite and/or mixture of metal oxides are reduced with hydrogen at a temperature of about 100° C. to about 500° C. for about 1 hour to about 5 hours in a hydrogen flow.

The oxidation can be performed by contacting a cycloalkane with molecular oxygen in the presence of the aforementioned composite metal oxide and/or mixture of metal oxides as a catalyst. The amount of the catalyst to be used may be in the range of from about 0.1 part by weight to about 50 parts by weight, and is preferably in the range of from about 0.5 part by weight to about 10 parts by weight, based on 100 parts by weight of the cycloalkane to be oxidized. The reaction temperature may be in the range of from about 0° C. to about 150° C., and is preferably in the range of from about 50° C. to about 130° C. The reaction pressure may be in the range of from about 0.01 MPa to about 10 MPa, and is preferably in the range of from about 0.1 MPa to about 2 MPa. A solvent can be employed in the oxidation reaction, if needed. Examples of the solvent include a nitrile such as acetonitrile and benzonitrile, a carboxylic acid such as acetic acid and propionic acid, and the like.

The post treatment operation after the oxidation is not particularly limited. Examples of the post treatment include a method comprising the steps of filtrating the reaction mixture to separate the catalyst, rinsing the reaction product with water, and then distilling the reaction product; and the like. When a cycloalkylhydroperoxide corresponding to a cycloalkane as a starting material is contained in the reaction mixture, the reaction mixture may be subjected to an alkaline treatment, reduction treatment or the like, to convert the cycloalkylhydroperoxide into a desired cycloalkanol or cycloalkanone. Namely, the process for producing a cycloalkanol and/or a cycloalkanone of the present invention may further comprise the step of converting the cycloalkylhydroperoxide into the cycloalkanol or cycloalkanone.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2003-337255 filed on September 29, including specification, claims and summary, are incorporated herein by reference in their entirety.

EXAMPLES

The present invention is described in more detail by following Examples, which should not be construed as a limitation upon the scope of the present invention.

Analysis of cyclohexane, cyclohexanone, cyclohexanol and cyclohexylhydroperoxide in a reaction solution were conducted by gas chromatography. Based on the results of the analysis, conversion of cyclohexane and respective selectivities to cyclohexanone, cyclohexanol and cyclohexylhydroperoxide were calculated.

Preparation of Catalysts

Reference Example 1

Into a 1 L beaker, 26.75 g (0.1 mol) of zirconyl(IV) nitrate dehydrate and 199.7 g of water were placed and were mixed with each other at a room temperature (about 25° C.) to prepare an aqueous solution thereof. Thereto, 54.77 g (0.1 mol) of diammonium cerium(IV) nitrate was added and was dissolved therein. Then, into the resultant solution, 36.14 g of 25% by weight ammonia water was added, to coprecipitate cerium and zirconium. After that, the water in the solution was evaporated. The residue obtained after the evaporation of the solution was calcinated at a temperature of 300° C. for 5 hours in the air atmosphere to obtain 28.8 g of the metal oxide containing cerium and zirconium as the metal elements therein with the molar ratio of cerium/zirconium of 1/1. The BET specific surface area of the oxide is 85 m²/g. The XRD analysis with copper Kα radiation shows no peaks of cerium oxide and zirconium oxide. This means that the previously defined solid solubilities of cerium oxide and zirconium oxide in the oxide are 100% and 100%, respectively.

Reference Example 2

Into a 1 L beaker, 26.74 g (0.1 mol) of zirconyl(IV) nitrate dihydrate and 229.19 g of water were placed and were mixed with each other at a room temperature (about 25° C.) to prepare an aqueous solution thereof. Thereto, 109.57 g (0.2 mol) of diammonium cerium(IV) nitrate was added and was dissolved therein. Then, to the resultant solution, 64.7 g of 25% by weight ammonia water was added, to coprecipitate cerium and zirconium. After that, the water in the solution was evaporated. The residue obtained after the evaporation of the solution was calcinated at a temperature of 300° C. for 5 hours in the air atmosphere, to obtain 48.49 g of the metal oxide containing cerium and zirconium as the metal elements therein with the molar ratio of cerium/zirconium of 2/1. The BET specific surface area of the oxide is 79 m²/g. The XRD analysis with copper Kα radiation shows no peaks of cerium oxide and zirconium oxide. This means that the previously defined solid solubilities of the cerium oxide and zirconium oxide in the oxide are 100% and 100%, respectively.

Reference Example 3

Into a 1 L beaker, 106.92 g (0.4 mol) of zirconyl(IV) nitrate dehydrate and 400 g of water were placed and were mixed with each other at a room temperature (about 25° C.) to prepare an aqueous solution thereof. Thereto, 109.57 g (0.2 mol) of diammonium cerium(IV) nitrate was added and was dissolved therein. Then, to the resultant solution, 98.8 g of 25% by weight ammonia water was added, to coprecipitate cerium and zirconium. After that, the water in the solution was evaporated. The residue obtained after the evaporation of the solution was calcinated at a temperature of 300° C. for 5 hours in the air atmosphere, to obtain 86.08 g of the metal oxide containing cerium and zirconium as the metal elements therein with the molar ratio of cerium/zirconium of 1/2. The BET specific surface area of the oxide is 103 m²/g. The XRD analysis with copper Kα radiation shows no peaks of cerium oxide and zirconium oxide. This means that the previously defined solid solubilities of the cerium oxide and zirconium oxide are 100% and 100%, respectively.

Reference Example 4

The metal oxide (4.69 g) obtained in Reference Example 1 was subjected to reduction treatment in a hydrogen flow at a temperature of 150° C. for 2 hours. The BET specific surface area of the oxide (4.6 g) obtained after the reduction treatment was 84 m²/g. The XRD analysis with copper Kα radiation shows no peaks of cerium oxide and zirconium oxide. This means that the previously defined solid solubilities of the cerium oxide and zirconium oxide are 100% and 100%, respectively.

Oxidation

Example 1

In a 200 mL stainless steel autoclave, 15 g (0.18 mol) of cyclohexane and 0.3 g of the metal oxide as a catalyst obtained in Reference Example 1 were placed, and the inside of the system was pressured to 0.6 MPa with nitrogen at a room temperature (about 25° C.), and then was pressured to 1.1 MPa with air. Thereafter, the temperature of the system was increased to 120° C. to oxidize the cyclohexane with the molecular oxygen in the air for 5 hours. After cooling, the resulting reaction solution was analyzed. As a result, the conversion of the cyclohexane was 1.4%, and the selectivities of cyclohexanone, cyclohexanol and cyclohexylhydroperoxide were 43.4%, 31.6% and 11.8%, respectively.

Example 2

Cyclohexane was oxidized with the molecular oxygen in the same procedure as in Example 1 except that the metal oxide obtained in Reference Example 2 was utilized as a catalyst instead of using the metal oxide obtained in Reference Example 1. As a result, the conversion of the cyclohexane was 1.0%, and the selectivities of cyclohexanone, cyclohexanol and cyclohexylhydroperoxide were 45.0%, 34.5% and 11.2%, respectively.

Example 3

Cyclohexane was oxidized with the molecular oxygen in the same procedure as in Example 1 except that the metal oxide obtained in Reference Example 3 was utilized as a catalyst instead of using the metal oxide obtained in Reference Example 1. As a result, the conversion of the cyclohexane was 1.8%, and the selectivities of cyclohexanone, cyclohexanol and cyclohexylhydroperoxide were 40.1%, 35.4% and 12.3%, respectively.

Example 4

Cyclohexane was oxidized with the molecular oxygen in the same procedure as in Example 1 except that the metal oxide obtained in Reference Example 4 was utilized as a catalyst instead of using the metal oxide obtained in Reference Example 1. As a result, the conversion of the cyclohexane was 3.6%, and the selectivities of cyclohexanone, cyclohexanol and cyclohexylhydroperoxide were 41.9%, 31.2% and 6.9%, respectively.

What is claimed is:

1. A process for producing a cycloalkanol and/or a cycloalkanone, the process comprising the step of:
   oxidizing cycloalkane with molecular oxygen in the presence of a mixture of metal oxides and/or a composite metal oxide, each containing cerium and zirconium as the metal elements therein.

2. The process according to claim 1, wherein the cycloalkane is cyclohexane.

3. The process according to claim 1 or 2, further comprising the step of:
   subjecting said composite metal oxide and/or mixture of metal oxides to a reduction treatment, prior to the oxidation step.

4. The process according to claim 1 or 2, wherein said composite metal oxide and/or mixture of metal oxides is selected from the group consisting of:
   a mixture of cerium oxide and zirconium oxide;
   a composite metal oxide of cerium and zirconium; and a mixture of said composite metal oxide and at least one metal oxide selected from cerium oxide and zirconium oxide.

5. The process according to claim 1, wherein the mixture of metal oxides and/or a composite metal oxide, each containing cerium and zirconium as the metal elements therein is a solid solution of cerium oxide and zirconium oxide.

* * * * *